United States Patent
Moharir

(10) Patent No.: US 9,344,686 B2
(45) Date of Patent: May 17, 2016

(54) METHOD, SYSTEM AND APPARATUS FOR TRANSCRIBING INFORMATION USING WEARABLE TECHNOLOGY

(71) Applicant: Vik Moharir, San Jose, CA (US)

(72) Inventor: Vik Moharir, San Jose, CA (US)

( * ) Notice: Subject to any disclaimer, the term of this patent is extended or adjusted under 35 U.S.C. 154(b) by 0 days.

(21) Appl. No.: 14/698,970

(22) Filed: Apr. 29, 2015

(65) Prior Publication Data

US 2015/0312533 A1    Oct. 29, 2015

Related U.S. Application Data

(60) Provisional application No. 61/986,056, filed on Apr. 29, 2014.

(51) Int. Cl.
| H04N 7/15 | (2006.01) |
| H04N 7/18 | (2006.01) |
| H04N 7/14 | (2006.01) |
| H04N 5/225 | (2006.01) |
| G06Q 50/24 | (2012.01) |
| G10L 15/26 | (2006.01) |

(52) U.S. Cl.
CPC .............. *H04N 7/185* (2013.01); *G06Q 50/24* (2013.01); *G10L 15/265* (2013.01); *H04N 5/2252* (2013.01); *H04N 5/2257* (2013.01); *H04N 7/142* (2013.01); *H04N 7/148* (2013.01)

(58) Field of Classification Search
CPC ............................... H04N 7/185; H04N 7/142
USPC ........................................................ 348/14.02
See application file for complete search history.

(56) References Cited

U.S. PATENT DOCUMENTS

| 2014/0222462 A1* | 8/2014 | Shakil | G06Q 10/0631 705/3 |
| 2014/0248838 A1* | 9/2014 | Hazell | H04M 1/6025 455/41.2 |
| 2014/0354758 A1* | 12/2014 | Spence | G06Q 10/10 348/14.01 |
| 2015/0127340 A1* | 5/2015 | Epshteyn | G10L 15/26 704/235 |
| 2015/0215753 A1* | 7/2015 | Leipzig | H04W 8/22 455/419 |

* cited by examiner

*Primary Examiner* — Creighton Smith
(74) *Attorney, Agent, or Firm* — Haverstock & Owens LLP

(57) ABSTRACT

A wearable scribing system includes glasses with a camera, speakers, a microphone and a display which communicate information to a remote system via a receiver/transmitter device. A scribe at the remote system inputs the information into an electronic health record. The wearable scribing system enables direct physician to physician communication.

35 Claims, 5 Drawing Sheets

METHOD, SYSTEM AND APPARATUS FOR TRANSCRIBING INFORMATION USING WEARABLE TECHNOLOGY

CROSS-REFERENCE TO RELATED APPLICATION(S)

This application claims priority under 35 U.S.C. §119(e) of the U.S. Provisional Patent Application Ser. No. 61/986,056, filed Apr. 29, 2014 and titled, "SCRIBELINK," which is hereby incorporated by reference in its entirety for all purposes.

FIELD OF THE INVENTION

The present invention relates to the field of the electronic health records. More specifically, the present invention relates to generating electronic health records using wearable technology.

BACKGROUND OF THE INVENTION

An Electronic Health Record (EHR) offers advantages over paper-based charts. However, EHRs suffer from a major drawback. The time required by physicians to enter information into the computer causes inefficiency and distracts attention away from the patient.

SUMMARY OF THE INVENTION

A wearable scribing system includes glasses with a camera, speakers, a microphone and a display which communicate information to/from a remote system via a receiver/transmitter device. A scribe at the remote system inputs the information into an electronic health record. The wearable scribing system enables direct physician to physician communication.

DETAILED DESCRIPTION OF THE PREFERRED EMBODIMENT

Figure 1:
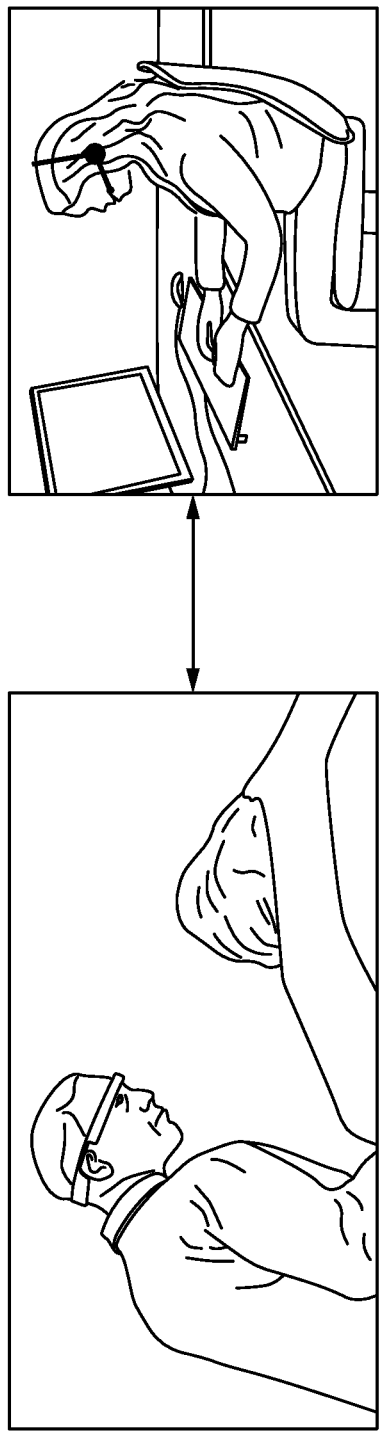
FIG. 1 illustrates images of a wearable scribing system according to some embodiments.

To overcome the problem of a doctor having to input information into a computer, a physician with smart glasses or another wearable communication device (e.g., Atheer Labs smart glasses, Google Glass®) has a real time connection to a scribe in a remote location as shown in FIG. 1. The physician wears a wearable scribing system which is able to acquire video and audio (e.g., using a video camera and a microphone) and a receiver/transmitter unit. The audio and video are transmitted to a scribe in a remote location (e.g., India) who enters the information into the electronic health record. In some embodiments, the scribe is able to communicate via audio and video with the physician.

The wearable scribing system includes an interface between a physician and a scribe. The physician has a wearable device (e.g., smart glasses with a video camera), an external microphone affixed to the smart glasses and a processing unit. In some embodiments, the processing unit is a device configured specifically for receiving and transmitting audio and video. In some embodiments, a waist pack contains a tablet computer/smart phone and an external battery pack, and these together serve as the processing unit. The smart glasses or wearable device interfaces with the receiver/transmitter via a wired connection or a wireless connection, such as Bluetooth®. The external microphone plugs into the headphone jack of the receiver/transmitter unit or communicates with the receiver/transmitter wirelessly. The receiver/transmitter relays the signals to the scribe via the Internet. In some embodiments, a single touch of an icon on the wearable device establishes the link between physician and scribe. In some embodiments, the link between the physician and scribe begins automatically upon startup of the wearable device and/or the receiver/transmitter or based on a voice command. In some embodiments, a server is used for buffering in between the receiver/transmitter and the scribe desktop computer. The receiver/transmitter is able to be worn anywhere (e.g., arm, wrist, leg). In some embodiments, the receiver/transmitter is not worn by the physician; rather, it is located in the room proximate to the wearable camera device.

The scribe documents into an EHR in real time as the physician performs a history and physical exam, discusses assessment and a plan with the patient, and in some instances verbalizes orders. The physician may elect to turn off the video feed but continue audio connection during the physical exam or vice versa, or turn off both.

The physician electronically signs orders on the wearable device or a computer of their choice. At the end of the visit, the scribe assigns billing and procedure codes to the encounter. The physician reviews the transcribed notes and billing codes and electronically signs the encounter as complete. This is able to be completed using the wearable scribing system or another computer. For example, the information input by the scribe is displayed on the display of the wearable scribing system, and the physician is able to use a voice command or a touch implementation on the wearable scribing system to electronically sign and/or make changes. The scribe marks the encounter as ready for billing.

Figure 2:
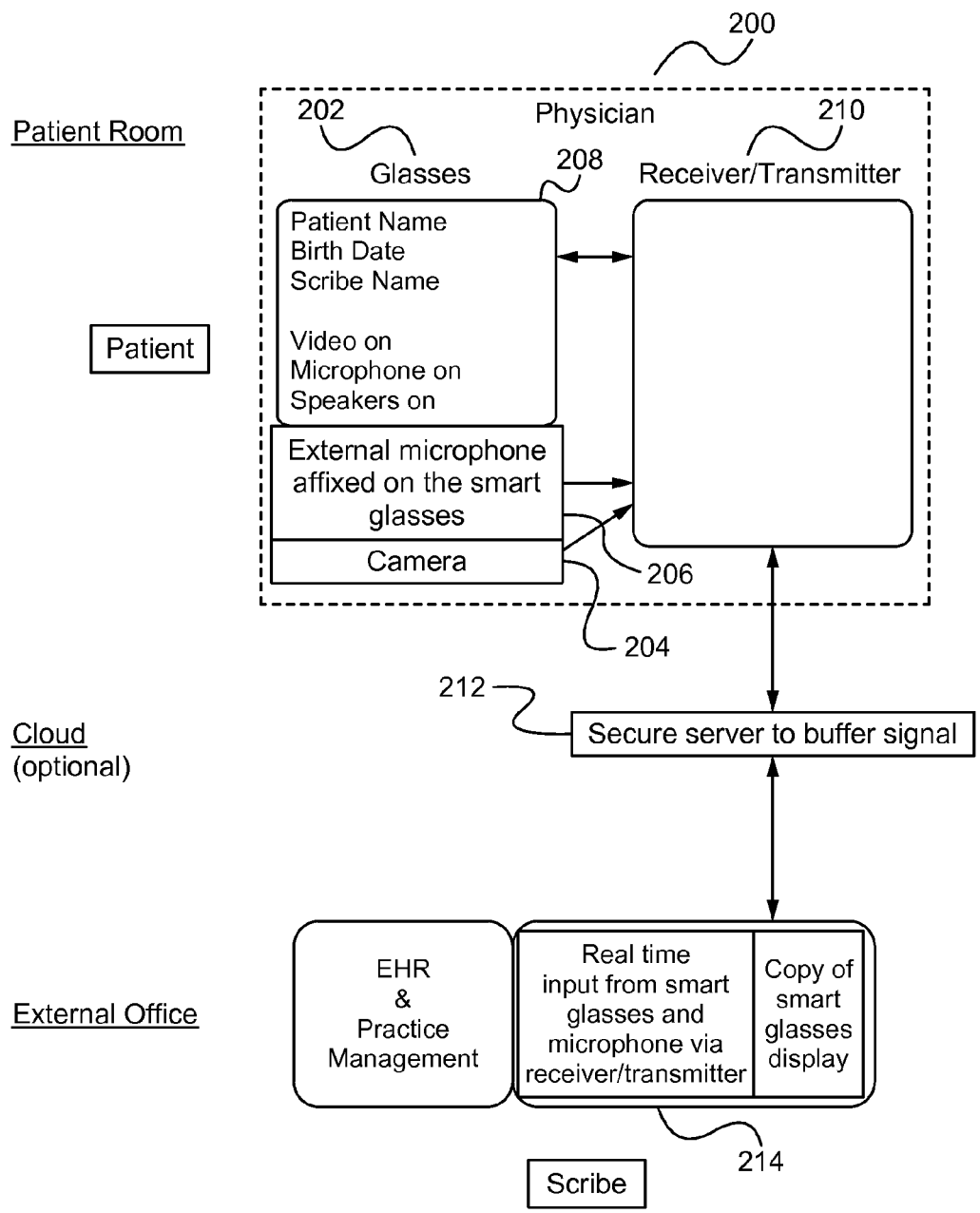
FIG. 2 illustrates a diagram of a wearable scribing system according to some embodiments.

FIG. 2 illustrates a diagram of the wearable scribing system according to some embodiments. In the patient room (or other clinical setting), a physician evaluates and treats a patient in the appropriate location: exam room, emergency department, procedure or operating room. The physician has a wearable scribing system 200. In some embodiments, the wearable scribing system 200 includes glasses 202 with a camera 204, a microphone 206 and a display 208 which communicate with a receiver/transmitter 210 (e.g., waist pack). In some embodiments, fewer or additional hardware is included such as a dedicated processor and/or additional circuitry. In some embodiments, the camera 204, the microphone 206 and/or the display 208 are attachable/detachable. In some embodiments, the glasses 202 are tethered to the receiver/transmitter 210 (e.g., the camera 204 and microphone 206 are wired to the receiver/transmitter 210), and in some embodiments, the glasses 202 communicate wirelessly to the receiver/transmitter 210. The receiver/transmitter 210 transmits and receives information via Wi-Fi and/or using any other network (e.g., cellular). For example, the receiver/transmitter 210 receives information from the camera 204 and microphone 206 and transmits that information to a server 212 in the cloud and/or to an external device 214 utilized by a scribe to receive/input the medical information (e.g., computer and headset).

The display 208 on the smart glasses wearable by the physician is able to display any of the following: patient name, patient birth date, indication whether the video output is on, indication whether the audio output is on, a live image of the scribe transmitted from the desktop camera of the scribe. This way the physician can be certain the scribe is interfaced. In some embodiments, the receiver/transmitter 210 includes a display, which, for example, is able to have any of the following icons: scribe link/unlink, video output on/off, video input on/off, audio output on/off and audio input on/off. In some embodiments, a full patient note is available for physician review on the smart glasses display for physician review and signature using the smart glasses. In some embodiments, the physician may access the full patient electronic health record and medical images using the smart glasses. In some embodiments, the smart glasses may be used for direct medical professional communications such as physician to physician or nurse to physician for the purposes of patient care. For example, captured content is able to be transmitted or shared between devices such as between professionals' computers or smart glasses. In some embodiments, the glasses 202 have touch sensors or buttons which toggle audio/video on/off, independently with a single touch.

In some embodiments, the cloud-based server 212 is used for a buffer in between the receiver/transmitter 210 and the device 214 of the scribe. This may allow for a smoother transmission but with the added cost of the cloud-based service.

At a remote location, a scribe has a device 214 (e.g., a desktop computer) and wears headphones with a microphone. In real time, the headphones put out the audio captured in the patient encounter. The scribe is able to use a microphone to communicate to the physician.

In some embodiments, a scribe computer screen displays the following: real time video from the smart glasses, a copy of the smart glasses display of the physician (so the scribe is aware of what the physician is viewing) and the electronic health record and practice management system with patient information. The scribe enters data in real time into software for physician review and signature.

In some embodiments, the wearable scribing system 200 includes smart glasses 202 (e.g., Atheer Labs smart glasses, Google Glass®), an external microphone 206 affixed to the smart glasses 202, and a waist pack. In some embodiments, the waist pack is solely composed of a dedicated receiver/transmitter unit. In some embodiments, the waist pack contains a tablet computer/smart phone as the receiver/transmitter 210 and an optional external battery pack. The smart glasses 202 interface to the receiver/transmitter unit or tablet via a wired or a wireless connection, such as Bluetooth®. The external microphone 206 plugs into the headphone jack of the receiver/transmitter unit or tablet/phone communicates wirelessly. The receiver/transmitter unit or tablet/phone transmits and receives information via Wi-Fi and/or using any other network (e.g., cellular).

In some embodiments, the wearable scribing system includes a setup process for small entities. A physician registers online and notifies a hosting company of the following: practice name and demographics, specialty, current EHR used, current Practice Management (PM) system used, current method of billing, do they wish for the host company to handle the PM system, smart glasses design request, requested start date, typical work schedule, the physician makes a credit card payment if they do not wish for the host company to handle PM, contract signed online, physician satisfaction survey-pre implementation, physician gives consent, with online signature, for the host company to have access to the EHR and PM of physician, the host company obtains access for scribes to document on the EHR and PM, the host company ensures that the EHR and PM has scribe functionality in that the scribe may enter notes and orders and indicate that they are ready for signature, the orders would not be official until reviewed and signed by a physician, the notes would not be official until reviewed and signed by a physician, work schedule created for scribes with extra 25% hours allocated to ensure continued coverage of physicians in case they exceed an anticipated schedule, physician schedule modified: training time blocked, day one of go live=50% volume, days two and three=66% volume, smart glasses, receiver/transmitter, batteries, charger, and cables sent to physician, link to online instruction for smart glasses fitting placed in package, practices notified on the importance of proper charging of batteries and having back up, instructions placed in package on checking for full Wi-Fi connectivity, one week prior to going live, physician performs and scribe make a test run with mock patient, and go live. In some embodiments, fewer or additional steps are implemented.

In some embodiments, the wearable scribing system includes a setup process for large entities. Organizations give names of all physicians, their specialty, typical schedule, and requested smart glasses style, organization name and demographics, current EHR used, current PM system used, current method of billing, do they wish for the host company to handle PM system, requested date to begin roll out and roll out schedule, organization makes credit card payment if they do not wish for the cost company to handle PM, contract signed online, physician satisfaction survey—pre implementation, organization gives consent, with online signature, for the host company to have access to the EHR and PM system, the host company obtains access for scribes to document on the EHR and PM, work schedule created for scribes with extra 25% hours allocated to ensure continued coverage of physicians in case they exceed anticipated schedule, physician schedule modified: training time blocked, day one of go live=50% volume, days two and three=66% volume, smart glasses, receiver/transmitter, batteries, charger, and cables sent to physician, link to online instruction for smart glasses fitting placed in package, practices notified on the importance of proper charging of batteries and having back up, instructions placed in package on checking for full Wi-Fi connectivity, one week prior to going live, physician performs and scribe make a test run with mock patient, go live as per roll out schedule, for large organizations, the host company provides a representative during roll out. In some embodiments, fewer or additional steps are implemented.

In some embodiments, the wearable scribing system includes a process for clinical use. The front desk registers the patient into the EHR, nurse places patient into a room (many clinics use medical assistants instead of nurses). Nurse takes the vital signs and obtains pertinent medical history (allergies, past medical history, safety screening) in the level of detail per facility protocol. Nurse enters the information into the EHR. The physician indicates to the scribe, who is based elsewhere (e.g., India), the patient they will see next or on whom they next wish to enter orders or dictate other documentation. The scribe, on their own desktop running the EHR software, opens the chart of the patient. All transmissions and aspects of the encounter and the host company adhere to HIPAA standards. A step in maintaining HIPAA compliance is to have the connectivity to the external system of the scribe as the only feature on the smart glasses. In some embodiments, all other applications such as email, recording, photos are disabled. A separate receiver/transmitter (e.g., tablet computer) that will provide wireless connectivity is provided. In some embodiments, the receiver/transmitter will also have all functions other than connectivity to the external system and EHR disabled. Prior to entering the room or once inside the patient room and after greeting the patient, the physician reviews the entered data as well as any necessary information from prior medical care. Unless specifically stated, the physician should perform all reviews on a device with which they feel most comfortable. Examples include: tablet computer, smart phone, and desktop. For efficiency, the device is located in the patient room or just outside the door. The device the physician uses for chart review should have rapid login capabilities with the scribing system automatically starting on login. The physician, wearing smart glasses, enters the room. The smart glasses will have clear lens so they can be used as part of the universal precautions against blood borne pathogens. The smart glasses have a HIPAA compliant secure video and voice link to the scribe. The image in the smart glasses display will have a live video of the scribe. This way the physician knows the scribe stands ready to document. The physician confirms identity of the patient by greeting them by name. For facilities that use wrist bands, the physician will look at the wrist band as well. The scribe will overlay the patient name, date of birth, and section being worked upon (history, orders, prescriptions, letter) on the smart glasses display. This permits the physician to know at all times the patient and section for which the scribe enters data. The physician obtains the patient history as usual and the scribe documents in real time. Prior to beginning the physical exam, the physician turns off the video feed originating from smart glasses but keeps on the audio as well as the smart glasses screen displaying the scribe and patient identification. "Video feed off" will appear in the display. During the physical exam, the physician will dictate as they examine and the scribe will continue to enter data—"HEENT exam is normal . . . the cardiac exam is normal . . . the lungs have faint wheezing in bilateral lower lobes . . . " Common sense is employed to maintain sensitivity. In the presence of the patient, the physician should not dictate items such as "the patient is a morbidly obese male appearing much older than stated age." The physician turns on the video feed to the scribe. The scribe continues to enter the note as physician performs subsequent steps. The physician discusses their assessment and treatment plan with the patient. The physician dictates orders for items such as medication, laboratory tests, and imaging. However, per The Joint Commission, these orders cannot be officially entered and carried out until reviewed and electronically signed by a physician [Joint Commission]. The physician reviews the orders entered by the scribe and electronically signs orders on a computer of their choice. If a patient, either the current one or one previously evaluated is not ready for discharge, the physician and scribe move onto next patient and repeat the steps above. As additional information becomes available, such as completed test results and recommendations from consulting physicians, the doctor and scribe ensure entry of these details into the EHR. If a patient is ready for discharge, the physician reviews the transcribed notes for accuracy. The scribe assigns a billing code to the visit and reviews with the physician to ensure they agree. If needed the physician can clarify the note to ensure the billing level matches the work performed. The physician signs the note as complete. The scribe immediately marks as ready for billing and submits for payment. After the patient visit, as additional information becomes available, such as follow up telephone conversations with the patient, completed test results, and recommendations from consulting physicians, the doctor and scribe ensure entry of these details into the EHR. The patient authorization to use the scribing system will be included in the general consent forms all patients sign, and the patient has the right to decline the use of the scribing system. In some embodiments, contingency plans are implemented. For example, a video recording of history and physical is directly stored in smart glasses with digital storage in the case of a connection loss to the scribe. The scribe will transcribe the encounter when the connection is reestablished or when the scribe is able to download the video file. In some embodiments where smart glasses are not available, the physician is able to dictate the encounter notes or the physician may also chose to type the note directly into the EHR. A paper and pen are able to be used in the case of full computer or electrical outage.

Figure 3:
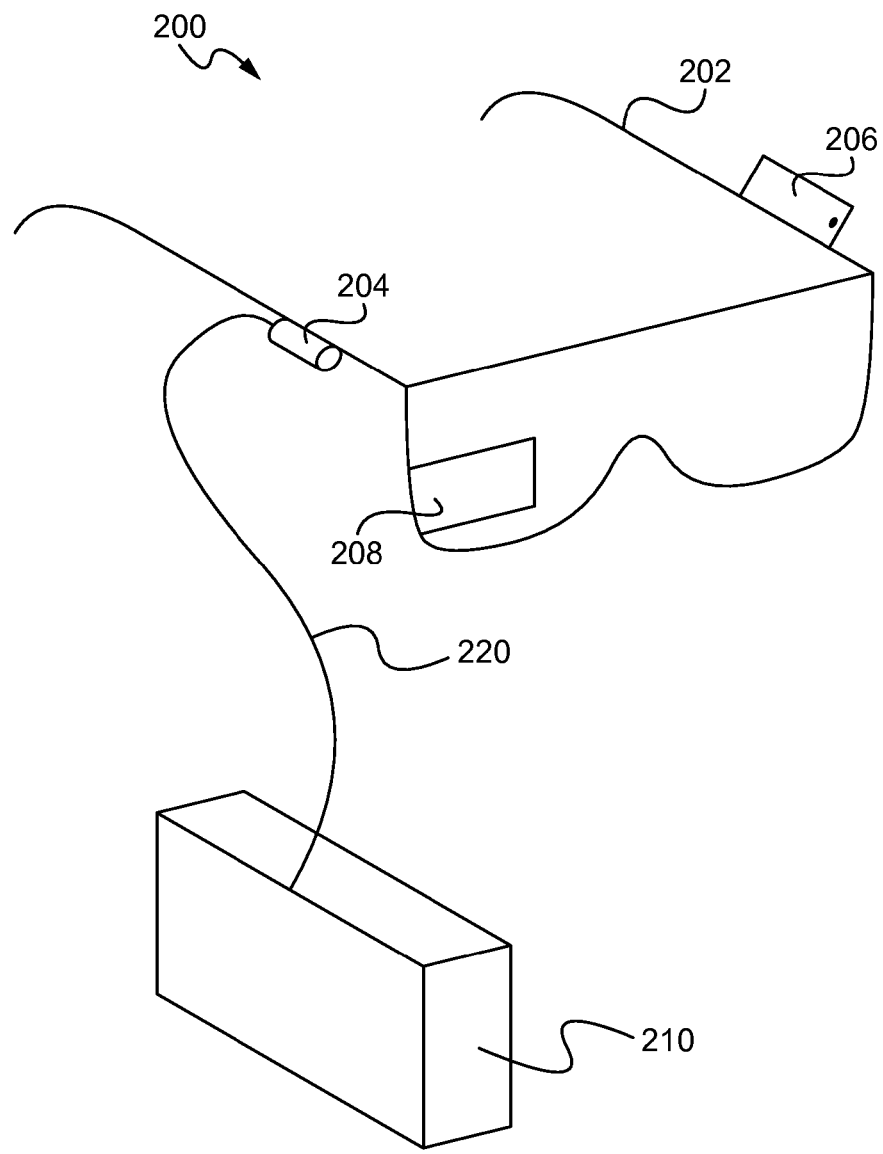
FIG. 3 illustrates a diagram of a wearable scribing system according to some embodiments.

FIG. 3 illustrates a view of the wearable scribing system 200 according to some embodiments. The wearable scribing system 200 includes glasses 202, a camera 204, a microphone 206, a display 208, a receiver/transmitter 210, and a tether/cable 220. The glasses 202 are able to be any shape, style and/or configuration. For example, the glasses 202 are able to have a single lens, multiple lenses or be goggles. A camera 204 and a microphone 206 are included with the glasses 202. In some embodiments, the camera 204 and the microphone 206 are detachable from the glasses 202, and in some embodiments the camera 204 and the microphone 206 are affixed to the glasses 202. The camera 204 and the microphone 206 are able to be positioned anywhere on the glasses 202 such as on the temples, the bridge, and/or the lens. In some embodiments, the camera 204 and the microphone 206 are a single component, and in some embodiments, they are separate components. A display 208 is also included anywhere on/in the glasses 202. For example, the display 208 is in front of part of one of the lenses of the glasses 202 so that a physician is able to easily view the display without being distracted from the non-display information in front of the physician. The tether 220 is able to be any type of wire or cable capable of communicating signals to/from the glasses 202 and the receiver/transmitter 210.

In some embodiments, the glasses 202 include wires within the glasses 202 to couple the receiver/transmitter 210 with the camera 204, the microphone 206 and the display 208. For example, the tether 220 couples with an internal wire which couples with the camera 204, the microphone 206 and the display 208.

The camera 204, the microphone 206 and the display 208 are able to communicate with the receiver/transmitter 210 via a tether 220 or wirelessly. For example, signals are sent to and from the camera 204, microphone 206, the display 208 and the receiver/transmitter 210 via the tether 220. In another example, the components have wireless capabilities and communicate using wireless transmissions.

The receiver/transmitter 210 is able to be any receiver/transmitter capable of receiving and transmitting information from/to devices such as the camera 204, the microphone 206 and the display 208. The receiver/transmitter 210 is also configured to receive and transmit information to a remote system (e.g., a computer be used by a scribe to electronically input information). In some embodiments, the receiver/transmitter 210 is configured to receive and transmit information to a cloud device which receives and transmits information to/from the remote system. The receiver/transmitter 210 is able to send information using wired or wireless communications. In some embodiments, the receiver/transmitter 210 encrypts information before sending information to the remote system so that only the intended recipient is able to access the information. In some embodiments, the receiver/transmitter 210 is a dedicated receiver/transmitter specifically designed for communicating with a scribe and wearable glasses with audio/video capabilities. In some embodiments, the receiver/transmitter 210 is a tablet computer, smart phone, smart watch, or another device.

The receiver/transmitter 210 is able to be configured to be worn on a user's belt with a clip, around their waist (e.g., in a waist pack), on their arm using an arm band, and/or any other location. In some embodiments, the receiver/transmitter 210 is not worn by the user.

Figure 4:
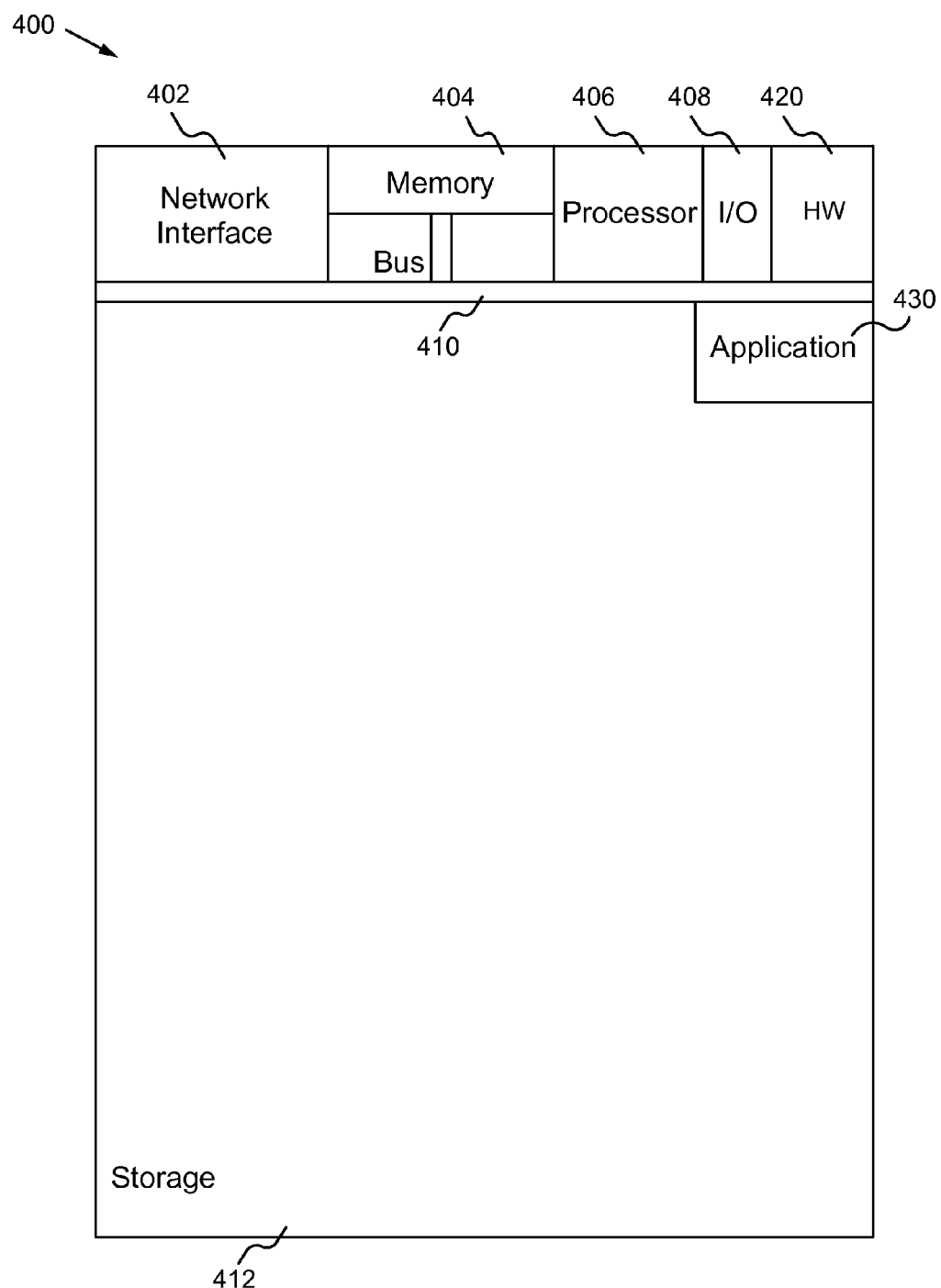
FIG. 4 illustrates a block diagram of an exemplary computing device configured to implement the wearable scribing system according to some embodiments.

In an exemplary implementation, a physician wears the glasses 202 for a patient consultation. The patient information is displayed on the display 208 for the physician to review while meeting with the patient. The conversation and the consultation with the patient is captured and recorded using the camera 204 and/or the microphone 206. The captured information is sent to the receiver/transmitter 210, and then the receiver/transmitter 210 sends the captured information to a remote system, where a scribe electronically inputs the information. In some embodiments, the wearable scribing system 200 includes fewer or additional components. For example, in some embodiments, there is no tether, and the camera 204, microphone 206 and display 208 communicate wirelessly with the receiver/transmitter 210. As described above, in some embodiments, the wearable scribing system 200 is able to utilize Google Glass® or other augmented reality devices to communicate information to a scribe. FIG. 4 illustrates a block diagram of an exemplary computing device configured to implement the wearable scribing system according to some embodiments. The computing device 400 is able to be used to acquire, store, compute, process, communicate and/or display information such as audio, images, videos and text. For example, the computing device 400 is incorporated with glasses to capture/send/receive/display information. In another example, the computing device 400 is a receiver/transmitter. In another example, the computing device 400 is a desktop computer configured for receiving/sending information from/to a receiver/transmitter as well as receiving input by a scribe. The computing device 400 is able to perform any of the methods/steps described herein. In general, a hardware structure suitable for implementing the computing device 400 includes a network interface 402, a memory 404, a processor 406, I/O device(s) 408, a bus 410 and a storage device 412. The choice of processor is not critical as long as a suitable processor with sufficient speed is chosen. The memory 404 is able to be any conventional computer memory known in the art. The storage device 412 is able to include a hard drive, CDROM, CDRW, DVD, DVDRW, High Definition disc/drive, ultra-HD drive, flash memory card or any other storage device. The computing device 400 is able to include one or more network interfaces 402. An example of a network interface includes a network card connected to an Ethernet or other type of LAN. The I/O device(s) 408 are able to include one or more of the following: keyboard, mouse, monitor, screen, printer, modem, touchscreen, button interface and other devices. Wearable scribing system application(s) 430 used to perform the wearable scribing system methods are likely to be stored in the storage device 412 and memory 404 and processed as applications are typically processed. More or fewer components shown in FIG. 4 are able to be included in the computing device 400. In some embodiments, wearable scribing system hardware 420 is included. Although the computing device 400 in FIG. 4 includes applications 430 and hardware 420 for the wearable scribing system, the wearable scribing system is able to be implemented on a computing device in hardware, firmware, software or any combination thereof. For example, in some embodiments, the wearable scribing system applications 430 are programmed in a memory and executed using a processor. In another example, in some embodiments, the wearable scribing system hardware 420 is programmed hardware logic including gates specifically designed to implement the wearable scribing system.

In some embodiments, the wearable scribing system application(s) 430 include several applications and/or modules. In some embodiments, modules include one or more sub-modules as well. In some embodiments, fewer or additional modules are able to be included.

Examples of suitable computing devices include a personal computer, a laptop computer, a computer workstation, a server, a mainframe computer, a handheld computer, a personal digital assistant, a cellular/mobile telephone, a smart appliance, a gaming console, a digital camera, a digital camcorder, a camera phone, a smart phone, a portable music player, a tablet computer, a mobile device, a video player, a video disc writer/player (e.g., DVD writer/player, high definition disc writer/player, ultra high definition disc writer/player), a television, an augmented reality device, a virtual reality device, a home entertainment system, smart jewelry (e.g., smart watch) or any other suitable computing device.

Figure 5:
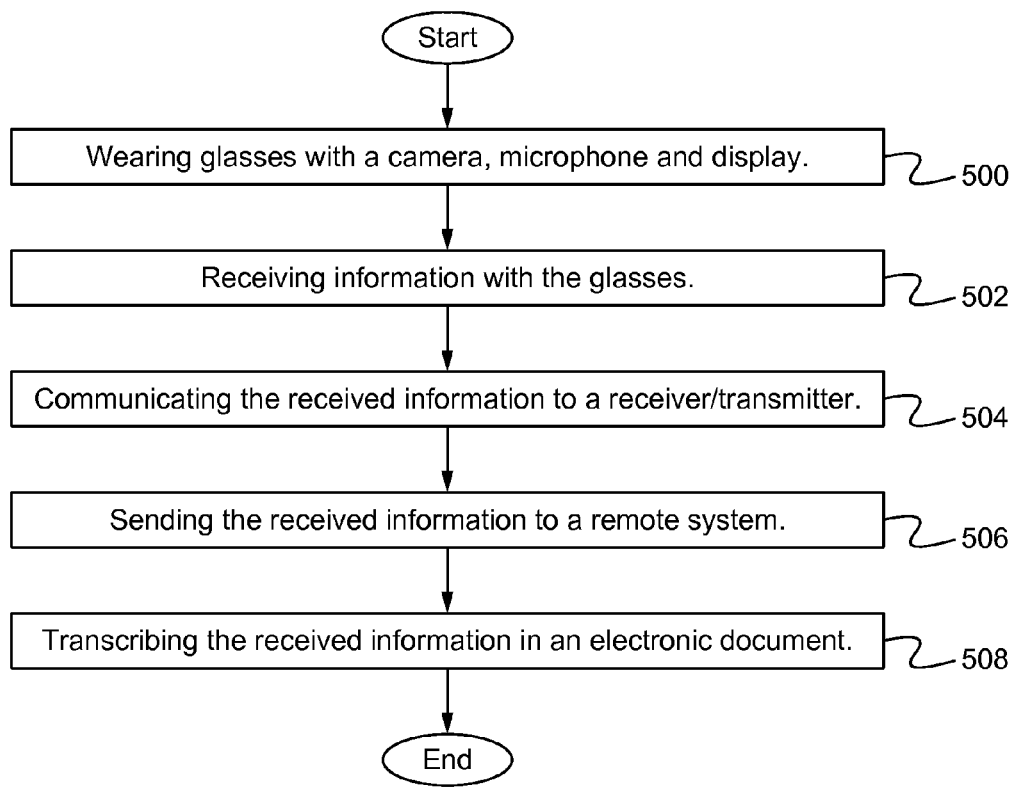
FIG. 5 illustrates a flowchart of a method of implementing the wearable scribing system according to some embodiments.

FIG. 5 illustrates a flowchart of a method of implementing the wearable scribing system according to some embodiments. In the step 500, a physician (or other user) wears the glasses with a camera, microphone and display and the receiver/transmitter. In some embodiments, there are one or more steps of initializing the glasses and the receiver/transmitter. For example, a button or the icon on the receiver/transmitter is pressed to turn on/link up the receiver/transmitter and the glasses. In the step 502, the glasses receive/capture information. For example, the camera of the glasses capture video, and the microphone captures audio (e.g., a patient describing a health concern to the physician). In the step 504, the glasses communicate the captured audio/video to the receiver/transmitter. In some embodiments, the receiver/transmitter includes a storage mechanism (e.g., internal memory) for storing the captured audio/video in case of transmission issues. In the step 506, the receiver/transmitter sends the audio/video to a remote location (e.g., to a computer and/or a scribe's headphones). In some embodiments, the receiver/transmitter sends the audio/video to a cloud device which sends the audio/video to the remote location. In the step 508, a user (e.g., scribe) transcribes what is in the audio/video into an electronic record. For example, the scribe types into a document or software application what the patient and/or physician say. In some embodiments, information goes back to the physician from the scribe such as video of the scribe at his computer via a webcam communicating with the receiver/transmitter which sends the video to the display of the glasses of the physician. In some embodiments, fewer or additional steps are implemented. In some embodiments, the order of the steps is modified.

To utilize the wearable scribing system, a physician wears the glasses with camera, microphone and display for any type of procedure or patient meeting. The glasses automatically acquire data and transmit the data to a remote system where a scribe inputs the information into an electronic document.

In operation, the wearable scribing system enables the physician to focus on the patient, rather than a computer running an EHR. The wearable scribing system permits doctors to function as doctors and not data entry specialists. By not having to write, type, or dictate, physician efficiency and job satisfaction will vastly improve. The wearable scribing system lets the scribe code the patient encounter for billing in a quicker and more thorough manner than current methods.

Although the wearable scribing system has been described relative to physicians, any user is able to utilize the wearable scribing system such as a police officer, an attorney, government employee and others.

The present invention has been described in terms of specific embodiments incorporating details to facilitate the understanding of principles of construction and operation of the invention. Such reference herein to specific embodiments and details thereof is not intended to limit the scope of the claims appended hereto. It will be readily apparent to one skilled in the art that other various modifications may be made in the embodiment chosen for illustration without departing from the spirit and scope of the invention as defined by the claims.

What is claimed is:

1. A method comprising:
    a. capturing video content and audio content using a wearable video acquisition device with a camera, a microphone and a display, wherein the video acquisition device enables a physician to review and sign a scribed patient note;
    b. communicating the captured video content and audio content from the video acquisition device to a wearable receiver/transmitter device;
    c. sending the captured video content and audio content from the receiver/transmitter device to a remote system;
    d. inputting electronic data related to the captured video content and audio content using the remote system to generate a scribed patient note; and
    e. providing an electronic signature on the scribed patient note using the video acquisition device.

2. The method of claim 1 wherein sending the captured video content and audio content to the remote system includes sending the captured video content and audio content to a cloud device which sends the captured video content and audio content to the remote system.

3. The method of claim 1 wherein sending the captured video content and audio content to the remote system includes sending the captured audio content to a headset of a scribe.

4. The method of claim 1 wherein the receiver/transmitter device comprises a self-contained unit, a smart phone or a tablet computer.

5. The method of claim 1 wherein the video acquisition device and the receiver/transmitter device communicate via a tether.

6. The method of claim 1 wherein the video acquisition device and the receiver/transmitter device communicate wirelessly.

7. The method of claim 1 wherein the receiver/transmitter device sends the captured video content and audio content to the remote system using a Wi-Fi network, a cellular network or a combination thereof.

8. The method of claim 1 wherein the display is configured to display scribe status information and patient information, including an electronic medical record of a patient.

9. The method of claim 1 further comprising sharing the captured video content and audio content for direct professional to professional communication for the purposes of patient care.

10. A system comprising:
    a. a wearable video acquisition device including a camera, a microphone and a display configured for capturing and displaying video content and audio content, wherein the video acquisition device enables a physician to review and sign a scribed patient note;
    b. a wearable receiver/transmitter device configured for receiving and transmitting the captured video content and audio content; and
    c. a remote system configured for receiving input based on the captured video content and audio content.

11. The system of claim 10 further comprising a cloud device configured for receiving the captured video content and audio content from the receiver/transmitter device and sending the captured video content and audio content to the remote device.

12. The system of claim 10 wherein the remote system includes a headset.

13. The system of claim 10 wherein the receiver/transmitter device comprises a self-contained unit, a smart phone or a tablet computer.

14. The system of claim 10 wherein the video acquisition device and the receiver/transmitter device communicate via a tether.

15. The system of claim 10 wherein the video acquisition device and the receiver/transmitter device communicate wirelessly.

16. The system of claim 10 wherein the receiver/transmitter device transmits the captured video content and audio content to the remote system using a Wi-Fi network, a cellular network or a combination thereof.

17. The system of claim 10 wherein the display is configured to display scribe status information and patient information, including an electronic medical record of a patient.

18. The system of claim 10 wherein the receiver/transmitter device is configured for sharing the captured video content and audio content with other devices for direct professional to professional communication for the purposes of patient care.

19. An apparatus comprising:
    a. a frame;
    b. a camera coupled to the frame;
    c. a microphone coupled to the frame;
    d. a display coupled to the frame;
    e. a non-transitory memory for storing an application, the application for:
        i. capturing video content and audio content using the camera and the microphone coupled to the frame which is wearable by a user;
        ii. displaying information using the display coupled to the frame, wherein the display enables a physician to review and sign a scribed patient note;
        iii. sending the captured video content and audio content to a wearable receiver/transmitter device configured to send the captured video content and audio content to a remote system for input into an electronic document; and
        iv. receiving information from the remote system to be displayed on the display; and
    f. a processor coupled to the memory, the processor configured for processing the application.

20. The apparatus of claim 19 wherein sending the captured video content and audio content to the remote system includes sending the captured video content and audio content to a cloud device which sends the captured video content and audio content to the remote system.

21. The apparatus of claim 19 wherein sending the captured video content and audio content to the remote system includes sending the captured audio content to a headset of a scribe.

22. The apparatus of claim 19 wherein the receiver/transmitter device comprises a self-contained unit, a smart phone or a tablet computer.

23. The apparatus of claim 19 further comprising a tether coupled between the camera, the microphone, the display and the receiver/transmitter device for communication.

24. The apparatus of claim 19 wherein the camera, the microphone, the display and the receiver/transmitter device communicate wirelessly.

25. The apparatus of claim 19 wherein the receiver/transmitter device sends the captured video content and audio content to the remote system using a Wi-Fi network, a cellular network or a combination thereof.

26. The apparatus of claim 19 wherein the display is configured to display scribe status information and patient information, including an electronic medical record of a patient.

27. The apparatus of claim 19 wherein the receiver/transmitter is configured for sharing the captured video content and audio content with other devices for direct professional to professional communication for the purposes of patient care.

28. An apparatus comprising:
   a. a camera;
   b. a microphone coupled to the camera;
   c. a display coupled to the camera, wherein the display enables a physician to review and sign a scribed patient note;
   d. a non-transitory memory for storing an application, the application for:
      i. capturing video content and audio content using the camera and the microphone which are wearable by a user; and
      ii. sending the captured video content and audio content to a wearable receiver/transmitter device configured to send the captured video content and audio content to a remote system for input into an electronic document; and
   e. a processor coupled to the memory, the processor configured for processing the application.

29. The apparatus of claim 28 wherein sending the captured video content and audio content to the remote system includes sending the captured video content and audio content to a cloud device which sends the captured video content and audio content to the remote system.

30. The apparatus of claim 28 wherein sending the captured video content and audio content to the remote system includes sending the captured audio content to a headset of a scribe.

31. The apparatus of claim 28 wherein the receiver/transmitter device comprises a self-contained unit, a smart phone or a tablet computer.

32. The apparatus of claim 28 further comprising a tether coupled between the camera, the microphone, and the receiver/transmitter device for communication.

33. The apparatus of claim 28 wherein the camera, the microphone and the receiver/transmitter device communicate wirelessly.

34. The apparatus of claim 28 wherein the receiver/transmitter device sends the captured video content and audio content to the remote system using a Wi-Fi network, a cellular network or a combination thereof.

35. The apparatus of claim 28 wherein the receiver/transmitter is configured for sharing the captured video content and audio content with other devices for direct professional to professional communication for the purposes of patient care.

* * * * *